United States Patent [19]

Jacobson

[11] Patent Number: 4,788,706

[45] Date of Patent: Nov. 29, 1988

[54] METHOD OF MEASUREMENT OF X-RAY ENERGY

[75] Inventor: Donald R. Jacobson, Milwaukee, Wis.

[73] Assignee: General Electric Company, Milwaukee, Wis.

[21] Appl. No.: 134,311

[22] Filed: Dec. 17, 1987

[51] Int. Cl.$^4$ .......................................... G01D 18/00
[52] U.S. Cl. ...................................... 378/207; 378/18; 250/252.1
[58] Field of Search .................... 378/4, 5, 18, 207; 250/252.1, 358.1

[56] References Cited

U.S. PATENT DOCUMENTS

| | | | |
|---|---|---|---|
| 4,323,782 | 4/1982 | Riihimaki et al. | 378/207 |
| 4,344,183 | 8/1982 | Jacobson | 378/207 |
| 4,352,020 | 9/1982 | Horiba et al. | 378/207 |
| 4,571,491 | 2/1986 | Vinegar et al. | 378/207 |
| 4,613,754 | 9/1986 | Vinegar et al. | 378/207 |
| 4,649,561 | 3/1987 | Arnold | 378/18 |

OTHER PUBLICATIONS

D. R. White; "The Measurement of Effective Photon Energy and Linearity in Computerized Tomography"; *British Journal of Radiology;* 1/80; pp. 5–11.
E. C. McCullough et al; "Performance Evaluation and Quality Assurance of Computed Tomography Scanners"; *Radiation Physics;* Jul., 1976, pp. 173–188.
R. J. Kriz et al; "An Investigation of Computer Tomography (CT) Linearity"; a pre-print believed to have been published in proceedings of Society of Photographic Instrumentation Engineers.
M. R. Millner et al; "Determination of Effective Energies in CT Calibration", *Medical Physics;* Nov/Dec., 1978, vol. 5, #6, pp. 543–545.
R. A. Rutherford et al; "Calibration and Response of an EMI Scanner", *Neuroradiology;* 1976; pp. 7–13.
D. R. Jacobson; "Quality Assurance for Computed Tomography Correlation with System Performance"; *Application for Optical Instrumentation in Medicine XI;* Apr., 1983; vol. 419, pp. 157–165.

*Primary Examiner*—Carolyn E. Fields
*Assistant Examiner*—John C. Freeman
*Attorney, Agent, or Firm*—James H. Beusse; Douglas E. Stoner

[57] ABSTRACT

X-ray energy in an x-ray beam is determined from a comparison of apparent absorption of energy by three different materials. Initially, the attenuation coefficients of each of the materials as a function of x-ray energy is determined. The ratios of attenuation coefficient differences between two of the materials and between one of the two materials and the third material are plotted over an energy range of interest. Thereafter, the materials are x-rayed and their absorption characteristics determined. The ratio between the differences in absorption characteristics is then calculated in the same manner as the ratio of attenuation coefficients. Matching ratios are then used to identify the energy level of the x-ray beam.

6 Claims, 2 Drawing Sheets

METHOD OF MEASUREMENT OF X-RAY ENERGY

This invention relates to x-ray systems and, more particularly, to a method and apparatus for measurement of effective energy of an x-ray beam.

In many x-ray systems such as, for example, computed tomography (CT) systems, images of an object or body are constructed from a matrix of data representative of the x-ray attenuation or absorption characteristics of the object or body in an x-ray beam. The data comprises computed attenuation with each entry in the matrix being a numerical value, e.g., a CT number which defines a gray scale pixel value for a reconstructed image. The relative values of the computed numbers enables generation of an image suitable for qualitative evaluation. However, since the computed attenuation, e.g., the CT numbers, are related to the effective energy of the x-ray beam, quantitative analysis requires prior knowledge of the effective x-ray energy of the beam. Furthermore, the effective energy also effects image contrast, i.e., relative difference in numerical values.

It is known that effective x-ray energy in keV (thousands of electron volts) is proportional to the voltage at the x-ray tube which develops the x-ray beam. Such voltage is commonly referred to as kVp in thousands of volts. Accordingly, one method of calibrating an x-ray system is to measure and adjust the kVp. However, such measurements are invasive, i.e., they require some connection to the x-ray voltage source and may affect the developed voltage since the current drawn by any measurement apparatus may be a significant fraction of the current produced by the x-ray power source. For example, x-ray sources may vary from 50 to 150 kVp and from 0 to 600 mA.

Another method of quntitative measurement of x-ray energy is set forth by D. R. White et al in an article entitled "The Measurement of Effective Photon Energy and 'Linearity' in Computerized Tomography" published in the *British Journal of Radiology*, vol. 53, pages 5-11, January, 1980. White et al propose an energy measurement system using a target containing mixtures of selected organic liquids stored in tubes and dispersed in a liquid filled container. Each of the organic liquid mixtures must have a linear attenuation coefficient ($\mu$) which varies more rapidly than that of the reference liquid material, typically water, in the container. The organic liquid mixtures are formulated from materials which have CT numbers spanning those found in a human body. In addition, the attenuation coefficient of the organic liquid mixtures must vary with energy such that they intersect the curve for water at specific energies within a range of interest, e.g., from 60 to 90 keV. By determining the attenuation coefficients for each organic liquid mixture using techniques well known in the art, it can be determined at what specific energies each of the liquids has the same coefficient as water. If an image is made of the composite target, the energy level of the x-ray beam can be determined by comparison of the relative CT numbers. That is, if water (the reference material) has the same CT number as one of the organic liquid mixtures, the energy level can be established from a chart of values by identifying the energy level at which that mixture has the same attenuation coefficient as water.

A disadvantage of the White et al procedure is that each of the organic mixtures must be carefully mixed from precisely measured components. Furthermore, the liquids are subject to evaporation and change with time so that frequent replacement is necessary. Still further, some of the liquids are hazardous and contact with the eye or skin can be harmful. Another disadvantage is that the liquids must be held in containers or vials and air entrapment avoided since air will give a false reading. Still another disadvantage is that the liquids are subject to mass density changes as a function of temperature requiring that their temperature be precise during measurement of x-ray energy. Still further, transportation of hazardous compounds creates other disadvantages.

SUMMARY OF THE INVENTION

It is an object of the present invention to provide a method for conveniently measuring effective energy of an x-ray system.

It is another object of the present invention to provide a method for determining the effective energy of an x-ray beam without direct measurement of x-ray voltage.

It is still another object of the present invention to provide a method for determining effective energy of an x-ray beam from information derived from an x-ray image.

The present invention is described with respect to a computed tomography system but may be employed with other types of x-ray systems. The invention is embodied in a method for determining the effective energy of an x-ray beam by providing an x-ray target incorporating three different materials, two of which have similar x-ray attenuation coefficient and a third which has an attenuation coefficient which varies substantially differently as a function of x-ray energy over a selected range of energies. The attenuation coefficients of each of the materials are determined over the range of interest and a ratio of the differences in coefficients is determined for a plurality of energy levels within the selected x-ray energy range. The x-ray target is then exposed to an x-ray beam and the numerical value of x-ray attenuation or CT numbers which are proportional to the attenuation values for each of the materials in the x-ray target are determined. The ratio corresponding to the difference in the numerical values of attenuation between the two reference materials and the difference in the numerical of attenuation between one of the reference materials and the third material is then computed. The resultant computed ratio is then compared to the previously determined ratios to identify values substantially equal to the computed ratios of numerical values of attenuation. Based upon the identified common values, the effective energy level of the x-ray beam can be determined as that energy level generating the common ratio. In a preferred embodiment, the two similar materials are plexiglass and water and the third dissimilar material is calcium hydroxyapatite with a density such that its attenuation coefficient falls between those of plexiglass and water over the energy range of interest.

DESCRIPTION OF THE DRAWINGS

For a better understanding of the present invention, reference may be had to the following detailed description taken in conjunction with the appended drawings in which.

DETAILED DESCRIPTION OF THE INVENTION

Figure 1:
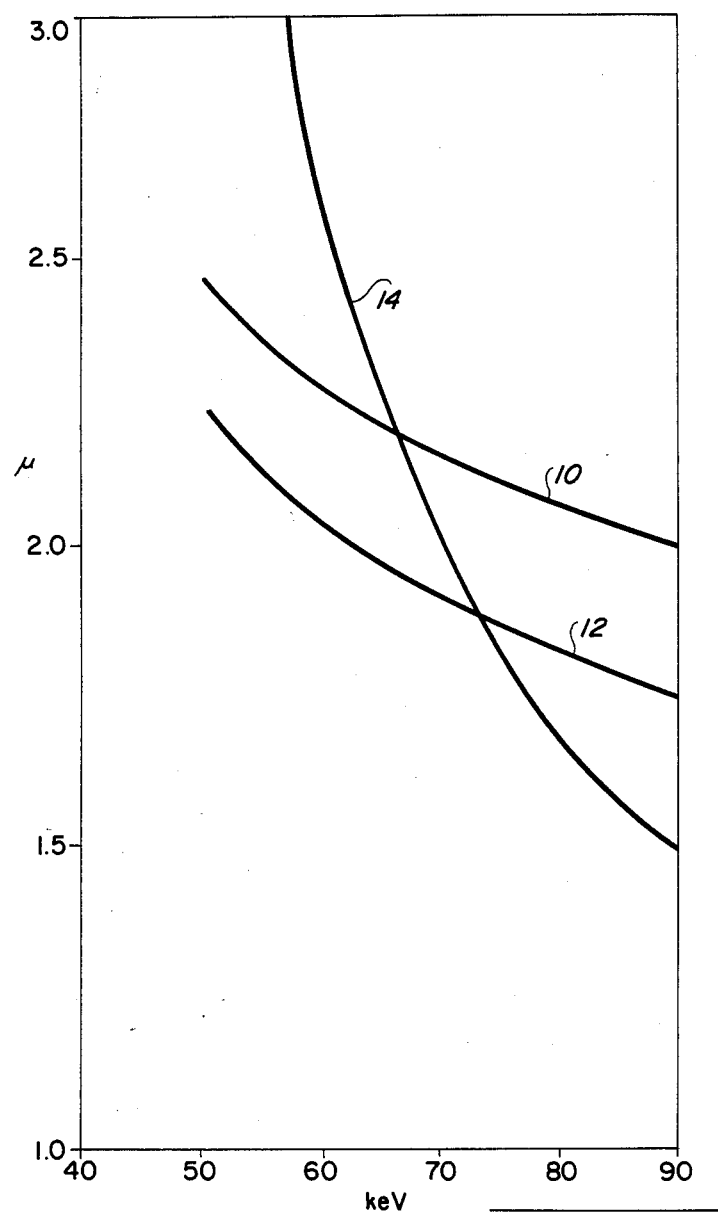
FIG. 1 is a graph illustrating variations in attenuation coefficients as a function of x-ray energy for three selected materials.

The present invention is described with particular reference to computed tomography (CT) but is applicable to other types of x-ray equipment and procedures. CT is the reconstruction by computer of a tomographic plane of an object, commonly referred to as a slice. An image of the plane or slice is developed from multiple x-ray absorption measurements made around the object's periphery, i.e., by a scan. Historically, attempts have been made to use the computer to analyze images. In computed tomography, the computer is used to synthesize images. The basic synthetic unit is the volume element. The CT slice is composed of many volume elements, each with its own characteristic absorption, which are displayed as a two dimensional image array or matrix of picture elements (pixels). Although the pixel of the display is two dimensional, it represents a three dimensional volume element which has a thickness equal to that of the tomographic slice. Pixels may be displayed as a hard copy computer print out of numerical values, referred to as CT numbers, which are proportional to the volume element absorption characteristics, or as a gray scale presentation on a cathode ray tube or display monitor where each pixel element is assigned a particular shade of gray depending upon its CT number.

CT equipment, i.e., x-ray systems which are used to generate a CT image, are well known. In general, the performance of a CT system is evaluated by use of various phantoms. A phantom is an object or target placed in a position to be scanned. A phantom may comprise a nylon object having a plurality of apertures in which polycarbonate rods are inserted. Since these two materials have an absorption coefficient which differs by approximately one percent, the CT system can provide an image in which the rods can be clearly seen.

While the CT systems are capable of providing clear images of objects which have very similar absorption characteristics, such absorption characteristics or attenuation characteristics are energy dependent. In some materials, the attenuation characteristic may vary at high rates as a function of x-ray energy while in other materials the attenuation characteristic may be less affected by variations in x-ray energy.

The CT system and other x-ray systems form an image of an object by detecting the x-rays which pass through the object. By establishing relative CT numbers or shades of gray as a function of the amount of x-rays detected through various portions of an object, an image of the object can be reconstructed.

The x-ray absorption characteristics of objects as a function of x-ray energy is a well known phenomena. The laws of radiation physics state that when a monochromatic x-ray beam of energy E passes through a small object of uniform density, it is attenuated according to the formula $I=I_o e^{-\mu L}$ where $I_o$ = the incident x-ray intensity, I = the transmitted intensity, L = the path length through the uniform density and $\mu$ = the linear attenuation coefficient at energy E. The attenuation coefficients of many common materials have been calculated and published values are readily found. In a CT system, the CT number is related to the linear attenuation coefficient by the equation CT number = k·$(\mu_a - \mu_b)/\mu_b$ where k is a magnifying constant, $\mu_a$ is the attenuation coefficient of the material being x-rayed and $\mu_b$ is the attenuation coefficient of a reference material, typically water, at the effective energy of the x-ray beam. Accordingly, there is a direct relationship between the attenuation coefficient and the CT number.

Applicant's invention takes advantage of the prior calculation and determination of attenuation coefficients for various materials. Turning now to FIG. 1, there is shown a graph illustrating the variation in attenuation coefficients of three selected materials as a function of x-ray energy. The graph labeled 12 is characteristic of water. The graph 14 represents calcium phosphate tribasic or calcium hydroxyapatite at a mass density of 0.66 gms per cc. The left side or Y-axis of the graph represents values of $\mu$ or x-ray attenuation coefficients while the x axis of the graph is calibrated in thousands of electron volts or keV. From the graph of FIG. 1, there can be computed a ratio of differences in attenuation coefficients over a range of interest, e.g., 60–90 keV. The ratio is established as a difference between the attenuation characteristics of two of the materials versus the difference in attenuation characteristics between two others of the materials. Typically, the ratio has a second term which is the difference between the attenuation coefficients of the two similar materials, i.e., plexiglass and water, and a first term which is the difference between one of the similar materials and the coefficient of the materials which has the rapidly changing attenuation coefficient. More particularly, a first term is formed by computing the difference in attenuation coefficients between plexiglass and calcium hydroxyapatite at a selected energy level and then dividing that number by the difference in attenuation coefficients between plexiglass and water at the same energy level. If, for example, the energy level is selected to be 70 keV, the first term becomes $(\mu_1 - \mu_2)$ representing plexiglass and calcium hydroxyapatite, respectively, which is equal to about (0.216−0.207) or about 0.009. The second term becomes $(\mu_1 - \mu_3)$ representing the attenuation coefficients of plexiglass and water, respectively, or about (0.216−0.192) or 0.024. The ratio is therefore, 0.009/0.024 or 0.375.

Figure 2:
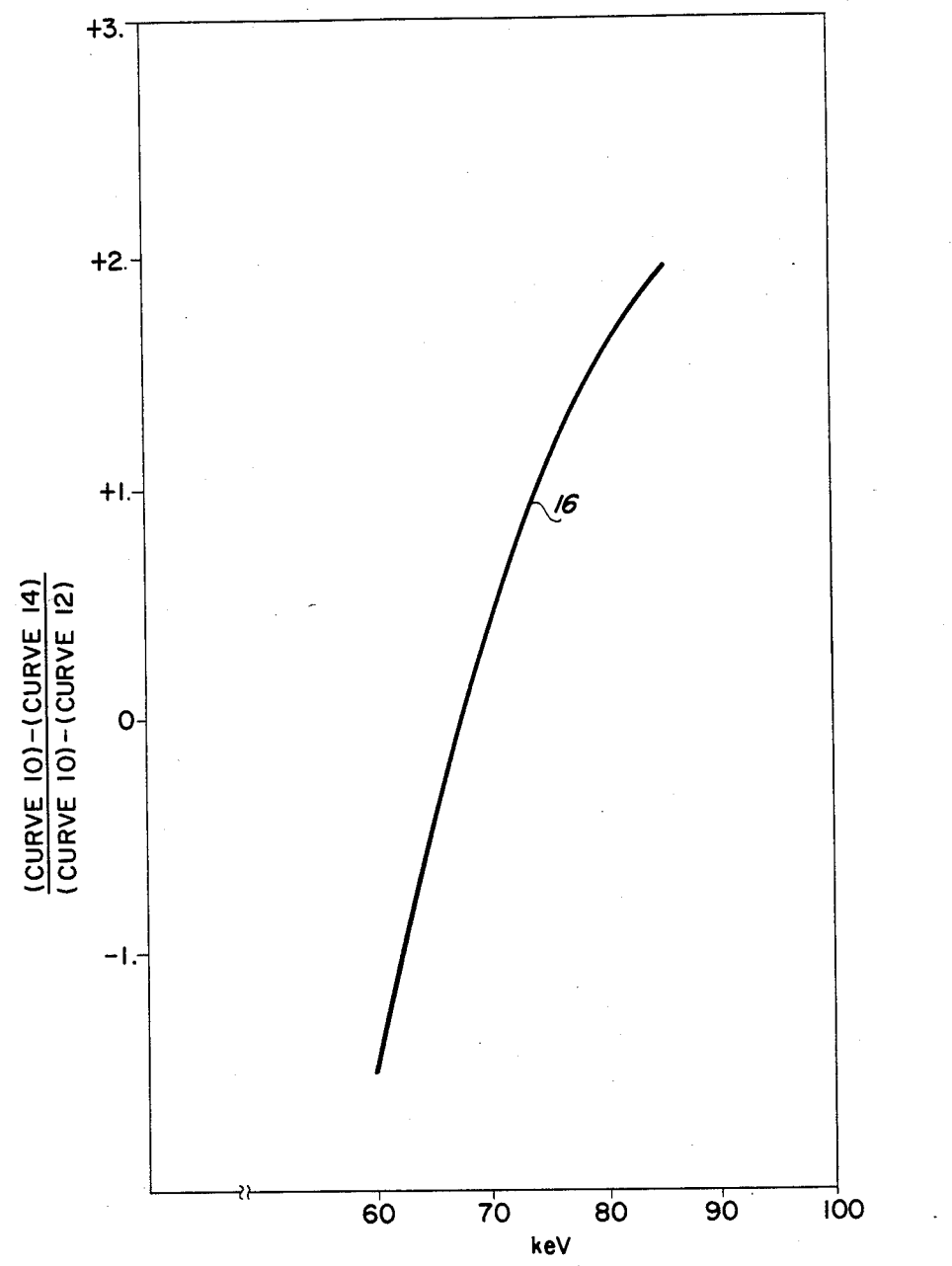
FIG. 2 is a graph of the ratios of attenuation coefficients of the materials in FIG. 1 as a function of x-ray energy.

Referring now to FIG. 2, there is shown another graph which illustrates a plot 16 of the ratios determined from the graph of FIG. 1. Referring particularly to the graph at 70 keV, it can be seen that the ratio appears as 0.375. It will, therefore, be apparent that by computing the ratio of attenuation coefficients over a selected range of keV, one can establish a single graph representing the change in the ratio as a function of x-ray energy.

In a CT system, as was pointed out above, the CT numbers are proportional to the attenuation coefficient $\mu$. If a phantom is now constructed utilizing inserts composed of the materials shown in FIG. 1, and a CT image of that object is obtained by scanning the object with a collimated x-ray beam, an average CT number will be provided by the system for each of the objects. By computing the ratios as described above for the CT numbers, one can then enter the graph of FIG. 2 with the computed ratio and identify the keV value associated with that ratio. Accordingly, such ratio provides an immediate method of measuring the effective energy of the x-ray beam.

Figure 3:
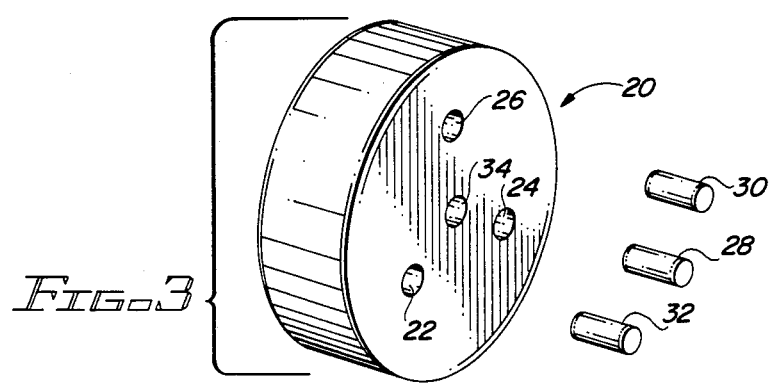
FIG. 3 is an illustration of an x-ray phantom for use in the practice of the present invention.

Turning now to FIG. 3, there is shown one form of x-ray phantom comprising a plastic disk 20 having multiple apertures for receiving inserts formed of selected x-ray absorbing materials. The phantom may be constructed with three apertures 22, 24 and 26, symmetrically positioned about the phantom for receiving the three inserts 28, 30 and 32 simultaneously. If the inserts or materials are positioned in the phantom for simultaneous exposure, only one image need be taken in order to obtain the CT numbers for each of the materials. Alternately, three images can be taken by placing the objects sequentially into a central aperture 34 in the phantom 20. It should be noted that it is desirable to symmetrically place the inserts into the phantom 20 in order to assure that the inserts are equally exposed to the x-ray energy. Since it is preferable to use water as one of the reference materials, the water may be stored in a container sized to fit into one of the apertures 22 through 26. While the method of physically calculating the ratios of CT numbers has been explained above, it will be apparent from observation of the phantom 20, that the relative position of the CT number of material 28 with respect to the CT numbers of materials 30 and 32 is a measure of the effective x-ray energy of the CT system. Of course, with suitable calibration, the effective x-ray energy can be converted to a value respresentative of kVp across the x-ray tube.

While the method has been described in terms of using plexiglass and water as materials having substantially similar attenuation coefficient variations with x-ray energy, other materials could be substituted so long as they meet the requirement that their variation with x-ray energy be substantially similar over the selected range of interest. The third material need be selected from those materials which have a significantly different variation in attenuation coefficient with x-ray energy and be produced with such a physical density so that its attenuation varies between that of the two reference materials over the energy range of interest. The characteristic of the third material, chosen to be calcium hydroxyapatite with a physical density of 0.66, is typical of the desired characteristic. Furthermore, the calcium hydroxyapatite is desirable since it very closely resembles the characteristics of human bone.

I claim:

1. A method for determining the effective energy of an x-ray beam at a predetermined spatial location comprising the steps of:
   providing an x-ray target incorporating a first and a second material having x-ray attenuation coefficients $\mu_1$ and $\mu_2$, respectively, which vary substantially similarly with variations in x-ray energy and a third material having an attenuation coefficient $\mu_3$ which varies at a faster rate than said first and said second materials as a function of x-ray energy;
   determining the attenuation coefficients of each of the first, second, and third materials over a range of known x-ray energy values;
   computing the ratio $(\mu_1-\mu_3)/(\mu_1-\mu_2)$ for a plurality of energy levels within a selected x-ray energy band;
   exposing the x-ray target to an x-ray beam of an unknown energy;
   determining a numerical value representative of x-ray attenuation for each of the first, second, and third materials in the x-ray target;
   calculating a ratio corresponding to a difference in numerical values of attenuation between said first and said second materials and a difference in numerical values of attenuation between one of said first and said second materials and the third material;
   identifying one of the ratios $(\mu_1-\mu_3)/(\mu_1-\mu_2)$ computed for a plurality of energy level having a value substantially equal to the calculated ratio of numerical values of attenuation; and
   determining from the identified one of the ratios $(\mu_1-\mu_3)/(\mu_1-\mu_2)$ the effective energy level of the x-ray beam.

2. The method of claim 1 wherein the step of exposing the target to an x-ray beam comprises the steps of:
   scanning the target with a collimated x-ray beam; and
   detecting x-rays passing through the target in a plurality of directions within a predetermined plane through the target.

3. The method of claim 2 wherein the step of determining numerical value comprises the step of:
   measuring the x-ray attenuation from the step of detecting for each of the directions relative to all other directions; and
   constructing a cross-sectional image giving a relative numerical value for the attenuation of each material in the scan.

4. The method of claim 1 wherein the step of providing an x-ray target includes the step of positioning each of said first, second and third materials in distinct, symmetrical positions within an x-ray phantom target.

5. The method of claim 1 wherein the step of providing an x-ray target includes the steps of successively positioning each of the three materials in a predetermined location within an x-ray phantom target and separately exposing each material to the x-ray beam.

6. A method for measuring x-ray energy in a computed tomography (CT) system comprising the steps of:
   providing a CT target using first, second, and third materials having predetermined x-ray attenuation coefficients, said first and second materials having similar attenuation variation as a function of x-ray energy over a predetermined range of energy, said third material having an attenuation characteristic which varies between that of said first and said second materials over the predetermined range;
   computing ratios of attenuation differences from the difference in attenuation between said first and said second materials at a plurality of selected energies within the predetermined range of energy and the difference in attenuation between one of said first and said second materials and said third material at each of the selected energies;
   exposing the target to x-rays in a CT machine and obtaining therefrom CT numbers for each of said first, second, and third materials;
   calculating a ratio of the difference between the CT numbers for said first and said second of the materials and the difference between the CT numbers of one of said first and said second materials and the CT number of said third material;
   identifying the ratio of the attenuation differences corresponding to the CT ratio; and
   identifying a corresponding x-ray energy from the identified ratio.

* * * * *